United States Patent [19]

Sugiyama et al.

[11] Patent Number: 4,822,907

[45] Date of Patent: Apr. 18, 1989

[54] METHOD FOR RECOVERING α-L-ASPARTYL-L-PHENYLALANINE METHYL ESTER

[75] Inventors: Katsumi Sugiyama; Takashi Yamashita; Toshihide Yukawa, all of Yokkaichi, Japan

[73] Assignee: Ajinomoto Co., Inc., Tokyo, Japan

[21] Appl. No.: 56,907

[22] Filed: Jun. 3, 1987

[30] Foreign Application Priority Data

Jun. 3, 1986 [JP] Japan ................................. 61-128405

[51] Int. Cl.$^4$ .......................................... C07C 103/52
[52] U.S. Cl. ..................................................... 560/41
[58] Field of Search ........................... 560/41; 530/801; 210/652, 653, 654, 655

[56] References Cited

U.S. PATENT DOCUMENTS

| | | | |
|---|---|---|---|
| 3,544,455 | 12/1970 | Adams et al. | 210/652 |
| 3,798,207 | 3/1974 | Ariyoshi et al. | 560/41 |
| 3,833,554 | 9/1974 | Ariyoshi et al. | 560/41 |
| 4,309,341 | 1/1982 | Kubo et al. | 560/41 |
| 4,601,829 | 7/1986 | Kaneko et al. | 210/652 |

FOREIGN PATENT DOCUMENTS 49180 4/1976 Japan ..................................... 210/652

Primary Examiner—Bruce D. Gray
Attorney, Agent, or Firm—Oblon, Fisher, Spivak, McClelland & Maier

[57] ABSTRACT

A process for recovering α-L-aspartyl-L-phenylalanine methyl ester from a solution containing various methyl ester or demethylated derivatives of α-L-aspartyl-L-phenylalanine methyl ester and chloride ions is disclosed. This process uses a reverse osmosis membrane having a specific chloride inhibition rate to desalt and concentrate a solution containing a specified ratio of δ-L-aspartyl-L-phenylalanine methyl ester to its derivatives until a specific weight ratio of organic chloride ion to the sum of α-L-aspartyl-L-phenylalanine methyl ester and its derivatives is obtained. This desalted and concentrated solution is then contacted with an aqueous solvent containing methanol and hydrochloride acid to recover high yields of α-L-aspartyl-L-phenylalanine methyl ester hydrochloride.

22 Claims, No Drawings

4,822,907

METHOD FOR RECOVERING α-L-ASPARTYL-L-PHENYLALANINE METHYL ESTER

BACKGROUND OF THE INVENTION

1. Field of the Invention

The present invention relates to a method for effectively recovering α-L-aspartyl-L-phenylalanine methyl ester (hereafter simply referred to as α-APM) from a solution mixture containing a methyl ester of the L-aspartic acid β-carboxyl residue of α-L-aspartyl-L-phenylalanine methyl ester (hereafter simply referred to as α-A(M)PM), the corresponding demethylated esters (α-APM, α-A(M)P) and α-L-aspartyl-L-phenylalanine (hereafter simply referred to as α-AP)) and an inorganic chloride.

2. Discusson of the Background

α-APM is a very useful substance to which considerable attention has recently been paid because it is a peptide, low calorie sweetener. α-APM is a methyl ester derivative of α-L-aspartyl-L-phenylalanine. Other methyl ester derivatives are also possible. These compounds have the following structures:

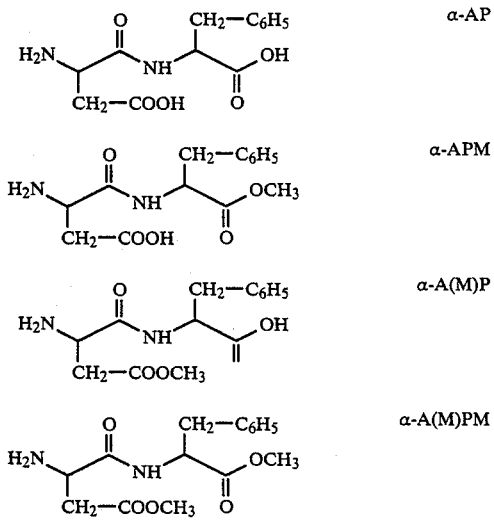

The properties of α-APM in an aqueous solution are such that it is relatively stable at temperatures lower than normal ambient temperatures, but under the severe conditions of high temperatures or in an acidic media, it readily undergoes various undesirable reactions. For example, α-APM can undergo demethyl-esterification to form α-AP. It can also undergo an intramolecular addition/elimination with loss of methanol to cyclize and form α-AP, or it can cyclize intramolecularly to form cyclized α-L-aspartyl-L-phenylalanine (hereafter simply referred to as DKP). All of these reactions are possible because α-APM is a methyl esterified 2 amino acid-long peptide.

Upon isolation and purification of α-APM from a reaction solution on an industrial scale, severe conditions of high temperatures or acidic conditions are often adopted to enhance the efficiency of the system. In such cases, by-production of undesired α-AP or DKP is unavoidable.

In addition, α-APM or α-AP can be methylated with methanol by-product to form α-A(M)PM or α-A(M)P. When α-APM is isolated and purified from reaction solutions, the formation of α-A(M)PM or α-A(M)P can occur not only in aqueous solutions but also, on many occasions, in solution mixtures of methanol and water. In this latter case, the formation of α-A(M)PM or α-A(M)P is even more accelerated.

Therefore, in producing α-APM, the process used suffers from the limitation that a part of α-APM changes to α-AP, DKP, α-A(M)PM or α-A(M)P during isolation and purification steps. This causes a serious reduction in the yield of α-APM, and results in that large quantities of valuable products are contained in the mother liquor from which α-APM is separated.

There are various processes for the synthesis of α-APM. These include a process which comprises reacting N-protected-L-aspartic anhydride and L-phenylalanine methyl ester in an organic solvent and then splitting the protective groups off in a conventional manner (see U.S. Pat. No. 3,786,039). Another process comprises directly reacting L-aspartic anhydride strong acid addition salts and L-phenylalanine methyl ester (Published Examined Japanese patent application No. 14,217/73). Still other such processes exist.

In any of these processes, the reaction solution obtained contains, in addition to α-APM, impurities such as the by-produced β-form, the unreacted L-phenylalanine and L-aspartic acid used as raw materials or by-products thereof. Therefore, a method for efficiently separating high purity α-APM in high overall yields is extremely important to the industrial production of α-APM. A notable such method comprises contacting impure α-APM with a hydrohalic acid in an aqueous solvent to precipitate the hydrohalic acid salt of α-APM. The salt is then subjected to solid-liquid separation and neutralization with an alkali to give α-APM (U.S. Pat. No. 3,798,207). With this method, the mother liquor remaining after the α-APM is isolated contains large quantities of salts, generally inorganic chlorides because hydrochloric acid is used as the hydrohalic acid because it is economical.

Accordingly, exhausted mother liquors obtained from the isolation and purification of α-APM from the industrial scale production of α-APM contain, in addition to α-APM a mixture of α-AP, DKP, α-A(M)PM, α-A(M)P and large amounts of inorganic chlorides. The inorganic chlorides vary depending upon the alkali used for the neutralization of the α-APM hydrochloride. Generally these are NaCl, NH$_4$Cl, KCl, etc.

Recovery, of α-APM from such a mother liquor is extremely advantageous in improving the overall industrial production yield of α-APM. This recovery contributes to great improvements in the yield at the isolation and purification step of α-APM and to a considerable reduction in α-APM production costs. However, it has heretofore been difficult to economically recover α-APM from such mother liquors advantageously because of the the following problems.

In order to improve the yield of the product, one recycles, to earlier steps, the mother liquor from which the product was once separated. This recycling operation enhances the concentration of the product in the mother liquor via evaporation, concentration, etc. One then again precipitates and separates the product from the mother liquor. This procedure can be repeated several times.

When large quantities of salts are contained in the mother liquor however, the concentrations of the salts becomes high and the salts are precipitated as the recycling procedure is repeated. In this case, it is difficult to recover the product in high yield and recycle the mother liquor, especially since it is advantageous to recover the α-APM product from economic hydrochloric acid solutions. With this system, the solubility of the inorganic chlorides decreases due to the hydrochloric acid present in the system so that it becomes more difficult to recover the product.

Therefore, in cases where salts (such as inorganic chlorides, etc.) are contained in large quantities, the solution must be previously desalted using any means available.

For such desalting operations, various methods are known. (1) For example, a method using ion exchange resins has been used. (2) A method which comprising adsorbing the product to an adsorbent such as a synthetic adsorbent, activated charcoal, etc., breaking the salts present through a non-adsorbed solution and then eluting with a polar solvent such as methanol, etc., has also been used. Other methods include (3) a method utilizing electric dialysis, and (4) a method using an ultrafiltration membrane, etc.

These methods suffer the common problem that large quantities of a secondary raw material is consumed for elution and regeneration of the ion exchange resins, the absorbents or the other desalting means. Complicated operations increase the costs of using systems (1) and (2). When the product has an electrolytic property, desalting is performed at the same time the product is dialyzed. This decreases the yield of (3).

Methods using an ultrafiltration membrane apply generally to products having a molecular weight of several thousands or more. In the case of products having a lower molecular weight, the product also permeates through the membrane so that the yield of the product is markedly reduced. In addition, the desalted solution thus obtained becomes dilute so that considerable energy is required to concentrate the solution to permit recovery of the product from the desalted solution. Therefore, recovery costs increase to the detriment of the economics of the overall system.

Another problem is that it is extremely difficult to crystallize α-APM directly from an impure system containing α-A(M)PM, α-A(M)P α-AP, DKP, in large quantities. The precipitation of α-APM crystals is inhibited by these impurities.

Accordingly, methods which comprises contacting such a solution with a strong acid such as HCl, H$_2$SO$_4$, etc. at high temperatures have been used to hydrolyze up to the constituent amino acids, fractionally crystallizing L-Phe and L-Asp, recovering each of these amino acids independently and then reusing them as raw materials.

With this method, the treatment required severe conditions of strong acids and high temperatures. This increases costs for equipment to ensure safe operation and resistance to corrosion. In addition, the method involves the consumption of large quantities of acids and alkalis.

There is thus a strongly felt need for an improved method for recovering α-APM from mother liquors and other industrially produced solutions containing α-APM together with other process impurities, such as α-APM derivatives and chloride ions.

SUMMARY OF THE INVENTION

Accordingly, it is an object of this invention to provide a novel method for recovering α-APM from solutions containing impurities resulting from the production of α-APM.

It is another object of this invention to provide a very effective method for thus recovering α-APM.

It is another object of this invention to provide a novel economic process for thus recovering α-APM.

The inventors have now surprisingly discovered such a method which satisfies all of the above objects of this invention, and other objects which will become apparent from the description of the invention given hereinbelow. This method comprises desalting and concentrating a specific solution containing α-APM using a reverse osmosis membrane.

The specific solution used (1) must contain α-L-aspartyl-L-phenylalanine (α-AP), α-L-aspartyl-L-phenylalanine methyl ester (α-APM), the methyl ester at the α-aspartic acid β-carboxy residue of α-L-aspartyl-L-phenylalanine (α-A(M)P) and the methyl ester at the L-aspartic acid β-carboxyl residue of α-L-aspartyl-L-phenylalanine methyl ester (α-A(M)PM) in the weight relation given by the following formula:

$$\frac{(I)}{(II)} = \frac{\alpha\text{-A(M)PM(grams)}}{\alpha\text{-AP(grams)} + \alpha\text{-APM(grams)} + \alpha\text{-A(M)P(grams)}} \leq 1$$

wherein:

α-AP is α-L-aspartyl-L-phenylalanine; α-APM is α-L-aspartyl-L-phenylalanine methyl ester;

α-A(M)P is the methyl ester at the L-aspartic acid β-carboxy residue of α-L-aspartyl-L-phenylalanine; and α-A(M)PM is the methyl ester at the L-aspartic acid β-carboxyl residue of α-L-aspartyl-L-phenylalanine methyl ester;

wherein this solution also contains the following weight ratio of chloride ion to dipeptide components:

$$\frac{(III)}{(I) + (II)} = \frac{Cl^-(g)}{\alpha\text{-AP(g)} + \alpha\text{-APM(g)} + \alpha\text{-A(M)P(g)} + \alpha\text{-A(M)PM(g)}} \geq 1$$

wherein:

Cl$^-$ represents the inorganic chloride content of this solution, and g=grams

The solution is desalted and concentrated using a reverse osmosis membrane having a sodium chloride inhibition rate of from 30 to 80% until the weight ratio of the inorganic chloride content to [(I)+(II)], that is to say until the ratio (III)/[(I)+(II)] becomes from 0.3 to 1.0. At this point the concentrate obtained is contacted with an aqueous solvent containing methanol and hydrochloric acid to cause the precipitation of α-APM. The precipitated α-L-aspartyl-L-phenylalanine methyl ester hydrochloride is then separated, and, if necessary, neutralized.

DETAILED DESCRIPTION OF THE PREFERRED EMBODIMENTS

The present inventors have found that by desalting and concentrating a specific solution, in which (1) the weight ratio of the α-A(M)PM content to the sum of α-APM, α-A(M)P and α-AP is not greater than 1.0 and (2) the weight ratio of inorganic chloride content to the sum of α-AP, α-APM, α-A(M)P, and α-A(M)PM is not less than 1.0, using a reverse osmosis membrane having a NaCl inhibition rate of 30 to 80% until the ratio of the inorganic chloride content becomes 0.3 to 1.0, then bringing the concentrate into contact with a methanol-hydrochloric acid aqueous solution and precipitating crystals of the α-APM hydrochloride, α-APM can be efficiently recovered from the solution in a high recovery yield.

One of the novel features of the present invention lies in using a reverse osmosis membrane having a low NaCl inhibition rate and then contacting the thus obtained desalted solution with an aqueous solution containing methanol and hydrochloric acid to crystallize the α-APM hydrochloride. This approach has been discovered to result in the effective recovery of α-APM from the aforesaid solution.

Another novel feature of this invention lies in specifying the amounts of α-A(M)PM and the inorganic chloride co-present. This system has been discovered to markedly improve the recovery rate of α-APM and at the same time, to make devices required for recovery extremely simple and miniature.

With respect to methods for effectively removing inorganic chlorides from a solution containing α-APM, α-A(M)P, α-AP, α-A(M)PM and inorganic chlorides, the present inventors have first made detailed investigations on the method for selectively removing inorganic chlorides alone. The inventors tried using various reverse osmosis membranes. They adjusted the NaCl inhibition rate of the membrane to low levels without any loss of valuable components. They payed attention to reverse osmosis membranes which have come to be widely used recently because of their economic advantages of being able to transform salt water into fresh water, and of being able to concentrate solutions containing valuable materials. Further with respect to a method for recovering α-APM from the desalted solution in a high yield, they have also extensively investigated a method capable of efficiently recovering α-APM from the solution in the highest yield throughout the desalting operation and α-APM recovering operation.

As a result, it has been found that regarding the desalting operation, when a membrane having a NaCl inhibition rate of 80% or more, water as a solvent is also permeated into a permeation liquid together with permeation of the inorganic chlorides and an absolute amount of the inorganic chlorides decreases if a lot of time is taken, but the amount of the concentrate is much reduced and due to an increased concentration of the inorganic chlorides in a non-permeation liquid, osmosis increases and becomes larger than the physical strength of the membrane. Thus renders the operation impossible. Further, the permeation rate of the inorganic chlorides markedly decreases due to the increased salt concentration, etc. It is thus difficult to perform this procedure a reverse osmosis membrane as having such a high NaCl inhibition rate on an industrial scale. By choosing the reverse osmosis membrane having adjusted the NaCl inhibition rate to not greater than 80%, the inorganic chloride co-present can be efficiently removed from the solution.

Furthermore, detailed investigations of valuable matters such as α-A(M)PM, α-APM, α-A(M)P, α-AP, etc. on their permeability has revealed that the permeability of these valuable matters is low. With a reverse osmosis membrane having a NaCl inhibition rate of approximately 30% or more, it is difficult for these materials to permeate into the permeation liquid at the same time as desalting is taking place, but the permeability of these valuable matters suddenly increases with a reverse osmosis membrane having a NaCl inhibition rate of approximately 30% or less. It is thus clear that for the purpose of the present invention, it is effective to use a reverse osmosis membrane having a NaCl inhibition rate of 30 to 80%.

The present inventors have also investigated the permeability of each of these valuable matters in detail and as a result, they have unexpectedly found that α-A(M)PM has an especially high permeability for reverse osmosis membranes notwithstanding the fact that α-A(M)PM has a larger molecular weight than α-APM, α-A(M)P and α-AP. Thus, when the ratio of α-A(M)PM content is relatively large in the desalting method of the present invention, it is disadvantageous that large amounts of α-A(M)PM, which is a valuable material be allowed to permeate into the permeation liquid accompanied by desalting increases and as the result, the recovery rate of α-APM from these valuable matters decreases. It has been found that in such a case, it is effective to demethyl-esterify α-A(M)PM co-present by means of heat treatment in a diluted hydrochloric acid aqueous solution under mild conditions, etc. to convert most of the α-A(M)PM into α-APM, α-A(M)P or α-AP having low permeability and then subjecting to the desalting according to the present invention, thus preventing loss of the valuable materials.

The reverse osmosis membranes which can be used in the desalting of the present invention include membranes of polysulfone-type, polyamide-type, cellulose acetate-type, etc. The NaCl inhibition rate of these membranes is adjusted to approximately 30 to 80%, but changes in the materials of the membranes is out of question.

The NaCl inhibition rate as used herein is a numerical value generally used to express the permeability of a solute and is calculated from a concentration of NaCl in a permeation liquid when a 0.2% NaCl solution is supplied to a permeation device having mounted thereto a reverse osmosis membrane under a pressure of 30 kg/cm²G at a temperature of 20° C., according to the following equation:

$$\text{Inhibition Rate} = \left(1 - \frac{\text{NaCl Concentration in Permeation Liquid}}{\text{NaCl Concentration in Raw Solution}}\right) \times 100 \ (\%)$$

The temperatures and pressures advantageously used in the desalting operation can vary depending upon the material of the membrane used. Ordinarily, appropriate operational conditions can be chosen, depending upon the specific properties of the membrane, from the temperature range of 5 to 50° C. and the pressure range of 10 to 70 g/cm²G.

The pH of the solution provided for the method of the present invention should be limited to a pH range corresponding to the pH durability of the membrane. The pH durability of the membrane varies basically depending upon materials of the membrane and operational temperature. Further the permeabilities of the inorganic chlorides, α-A(M)PM, etc. change more or less depending upon pH. Therefore, it is desired to experimentally determine the pH range correspondingly the ratios of their contents. In general, pH ranges from 2 to 8 can be used, taking the foregoing into account.

Next, the present inventors have made various investigations on a method for recovering α-APM from the thus obtained desalted solution. It has thus been found that in order to recover α-APM from an impure solution containing, in addition to α-APM, α-A(M)PM, α-A(M)P or α-AP in a high yield, the most advantageous method comprises contacting the solution with an aqueous solution containing methanol and hydrochloric acid to cause the crystallization of α-APM hydrochloride. The hydrochloride is then subjected to solid-liquid separation and α-APM is recovered as the α-APM hydrochloride crystals (U.S. Pat. No. 3,798,207).

As a result of further detailed investigations on this crystallization step of the process of the present invention, it has been found that the recovery ratio of α-APM decreases to cause disadvantages as the ratio of the α-A(M)PM content in the desalted solution. Therefore, the present inventors have made investigations on his fact in further detail and as a result, they have found that upon crystallization of the α-APM hydrochloride by contacting with the aqueous solution containing methanol and hydrochloric acid, a long time is required to obtain good yields of α-APM when α-A(M)PM is present in large quantities. This is due to their discovery that the rate of conversion of α-A(M)PM into α-APM in solution is slow as compared to the rate of conversion of other peptides, i.e., α-A(M)P and α-AP into α-APM. When the crystallization step is performed in industrial production, most of α-A(M)PM is not converted into α-APM but remains in the solution. This decreases the recovery rate of α-APM.

In view of the foregoing facts, one of the features of the present invention lies in that by specifying the ratio of α-A(M)PM content in the solution provided for the recovery method according to the present invention, loss of α-A(M)PM upon desalting is avoided and at the same time, the solution is brought into contact with the aqueous solution containing methanol and hydrochloric acid to recover α-APM a the α-APM hydrochloride. With this approach the efficiency of the system is markedly improved and the crystallization device used is miniaturized. Both of these factors contribute to an overall great reduction in device costs.

The present inventors have further made careful investigations on the amount of the inorganic chlorides which affect the recovery rate upon recovery of α-APM as the α-APM hydrochloride. They have found that when the weight ratio of inorganic chloride content to valuable material content, such as α-APM, etc. is approximately 0.3 to 1.0 by weight, even though desalting is not performed as excessively as 0.3 or less, the rate of recovery of α-APM is very high rate. When this ratio is 1.0 or more, the inorganic chlorides are precipitated upon the crystallization of the α-APM hydrochloride. In order to avoid such precipitation, water or the like should be added from an external source to dissolve the inorganic chloroides. In such a case, the concentration of α-APM and its derivatives is decreased and the crystallization rate of the α-APM hydrochloride decreases and the recovery rate of α-APM decreases.

Another feature of the present invention resides in that when the solution provided for the recovery method of the present invention, in which the ratio of the inorganic chloride content to the total sum of the valuable material (such as α-APM and the like) is not less than 1.0 in a weight ratio, is desalted up to a 0.3 to 1.0 weight ratio, using the reverse osmosis membrane having a NaCl inhibition rate of 30 to 80%, one avoids increase in desalting load due to excessive desalting. Taking advantage of this fact results in reduction in equipment costs and operation costs because of a cutback in the desalting installation.

It is desired that the amount of methanol used in the present invention be experimentally determined in a range of about 2 mols or less per 1 liter of desalted solution. This amount of methanol varies somewhat since the suitable amount varies depending upon the ratios of α-A(M)PM, α-APM, α-A(M)P and α-AP contained in the desalted solution. When the amount of methanol exceeds about 2 mols per 1 liter of desalted solution, methyl-esterification of α-APM is accelerated to increase the formation of α-A(M)PM so that the recovery rate of α-APM is reduced. When the amount of methanol is as short as less than 1 mol per 1 mole of α-AP, the recovery rate of α-APM is reduced.

It is necessary that the amount of hydrochloric acid be appropriately determined and used in such a range that the inorganic chlorides co-present in the desalted solution do not precipitate. It is generally preferred that the hydrochloric acid be present in the range of about 0.5 to about 5 mols per 1 liter of the desalted solution and in an amount at least equimolar to the total mole number of α-A(M)PM, α-APM, α-A(M)P and α-AP. This increases the yield.

Other solvents that do not inhibit the addition of α-APM to hydrochloric acid, for example, ethylene glycol, acetone, etc. may also be incorporated in such an amount that they do not markedly reduce the solubility of the inorganic chlorides upon crystallization of the α-APM hydrochloride by contacting with the aqueous solution containing methanol and hydrochloric acid. In any event, examination and determination of optimum condition within the given conditions can be easily made by one skilled in the art.

Other features of this invention will become apparent in the course of the following descriptions of exemplary embodiments which are given for illustration of the invention and are not intended to be limiting thereof.

EXAMPLE 1

A raw solution having pH of 4.54 and containing 8.7 g of α-A(M)PM, 5.3 g of α-APM, 2.9 g of α-AP and 27.3 g of NaCl per 1 liter of solution was supplied to a permeation device having mounted thereto spiral polyamide reverse osmosis membranes having NaCl inhibition rates of 80, 60, 30% and 15% (control), respectively, at a temperature of 20° C. under a pressure of 40 kg/cm$^2$. Desalting and concentration were performed, while cyclizing and mixing a non-permeation solution to and with the raw solution.

From the composition of the permeation liquid exhausted in this case, the inhibition rate of each component was calculated according to the following equation.

$$\text{Inhibition Rate (\%)} = \left(1 - \frac{\text{Concentration in Permeation Liquid}}{\text{Concentration in Solution Supplied}}\right) \times 100$$

The results are shown in Table 1. Analysis method: liquid chromatography (α-A(M)PM, α-APM, α-AP), (Cl−).

TABLE 1

| Inhibition Rate | Kind of Membrane Inhibition Rate of NaCl (%) | | | |
|---|---|---|---|---|
| | 80 | 60 | 30 | 15 (control) |
| Immediately after permeation started: | | | | |
| NaCl | 85.6 | 60.3 | 23.5 | 11.0 |
| α-A(M)PM | 93.1 | 91.0 | 82.7 | 56.7 |
| α-APM | 99.0 | 99.1 | 96.2 | 74.1 |
| α-AP | 99.7 | 99.5 | 98.8 | 81.5 |
| When concentrated to 2.5 times: | | | | |
| NaCl | 82.3 | 56.5 | 19.4 | 9.3 |
| α-A(M)PM | 93.9 | 92.2 | 84.1 | 59.3 |
| α-APM | 99.6 | 99.3 | 97.7 | 79.2 |
| α-AP | 99.9 | 99.7 | 98.3 | 85.6 |

From this example, it can be seen that when the NaCl inhibition rate of the reverse osmosis membrane is lower than 30%, the recovery rate of the vauable material is seriously reduced. At the same time, it is also evident that α-A(M)PM in the valuable material is specifically readily permeable notwithstanding that its molecular weight is large.

EXAMPLE 2

While cooling, 28% NH₃ water was added to a mother liquor obtained by separating α-APM hydrochloride, which contained 0.89% of α-APM, 1.54% of α-A(M)PM, 0.31% of α-A(M)P, 0.48% of α-AP and 12.6% of HCl to neutralize the solution to a pH of 5.2. The neutralized solution was supplied to a flat membrane type permeation device having having mounted thereon a polyamide type reverse osmosis membrane (A) having a NaCl inhibition rate of 50% and for comparison polysulfone type reverse osmosis membrane having the NaCl inhibition rate of 25%, respectively, at a temperature of 25° under a pressure of 40 kg/cm²G. While cyclizing a non-permeation liquid to a neutralizing liquid tank for supplying to the permeation device, the solution was desalted and concentrated until the volume of the neutralizing liquid became the original volume. Next, water was added until the volume became the original volume. Further by repeating similar operation, the system was desalted and concentrated until the volume became half of the original volume. The results are shown in Table 2.

TABLE 2

| Residual Rate | Kind of Membrane | |
|---|---|---|
| | Polyamide Type (A) | Polysulfone Type (B) |
| α-APM | 98.0% | 60.8% |
| α-A(M)PM | 80.3% | 48.2% |
| α-A(M)P | 97.8% | 60.8% |
| α-AP | 98.7% | 68.9% |
| NH₄Cl | 50.4% | 32.5% |

From this example, it can be seen that the results are the same as in Example 1.

EXAMPLE 3

1.5 liters of a solution containing 9.2 g of α-APM, 26.8 g of α-A(M)PM, 7.6 g of α-AP, 2.2 g of α-A(M)P and 38 g of NaCl per 1 liter of the solution was treated to reduced pressure until the volume was reduced to 0.6 liters. The concentrate was divided into 3 aliquots (A, B and C), each of which was charged in a 500 ml 3-necked flash equipped with a stirrer. Methanol, 8 ml, and 43 ml of 35% hydrochloric acid were added to A and 10 ml of 35% hydrochloric acid was added to B. Each mixture was heated at 40° C. for 2 hours to demethyl-esterify approximately 20% of the α-A(M)PM. Then, 8 ml of methanol and 33 ml of 35% hydrochloric acid were added. To C was added 20 ml of 35% hydrochloric acid and the mixture was heated at 40° C. for 4 houss to demethylesterify approximately 75% of αA(M)PM. Then, 8 ml of methanol and 23 ml of 35% hydrochloric acid were added thereto. Next, each mixture was put in a thermostat adjusted to 10° C. to perform crystallization for 3 days with stirring. The precipitated crystals were taken by filtration. After washing with a small amount of cold 2 N hydrochloric acid, the crystals were dried at 50° C. under reduced pressure.

Infrared absorption spectra of these crystals were identical with those of α-APM hydrochloride. The results on yield, recovery rate and purity (liquid chromatography) are shown in Table 3.

TABLE 3

| No. | I/II Ratio in Raw Solution | Yield (g) | Purity (%)*[2] | Recovery Rate (%)*[3] | Concentration of α-A(M)PM Remainded in ML (g/dl) |
|---|---|---|---|---|---|
| A | 1.4 | 24.1 | 92.5 | 39.8 | 2.72 |
| B | 0.9 | 30.4 | 97.5 | 52.9 | 1.42 |
| C | 0.2 | 33.2 | 98.1 | 58.1 | 0.62 |

[1](mol number of α-A(M)PM)/(sum of mol numbers of α-APM, α-A(M)P and α-AP)

*[2]Purity as α-APM hydrochloride dihydrate

*[3]Recovery Rate (%) = $\frac{\text{(Mol number of α-APM in crystals)}}{\text{Total mol number of α-APM, α-A(M)PM, α-A(M)P and α-AP in raw solution}} \times 100$ From this example, it can be seen that when the I/II ratio in the raw solution provided for the crystallization step is greater than 1.0, the yield of α-APM as the product is markedly reduced.

EXAMPLE 4

α-APM was crystallized by neutralizing impure α-APM hydrochloride containing 2.2% of α-AP and 3.4% of α-A(M)PM. The thus obtained mother liquor was further concentrated and again subjected to crystallization of α-APM. The mother liquor (composition: 0.95 g/dl of α-APM, 0.77 g/dl of α-AP, 0.97 g/dl of α-A(M)PM, 0.22 g/dl of α-A(M)P, 0.17 g/dl of DKP and 5.9 g/dl of NH₄Cl, pH 4.9) obtained by separating α-APM underwent repeated concentration and dialysis operation in a manner as described in Example 2, using a polyamide type reverse osmosis membrane having a NaCl inhibition rate of 50%. Thus, 4 kinds of the treated solutions having various desalting rates of NH₄Cl were obtained.

The results are shown in Table 4.

TABLE 4

| No. | Treated Solution | | | |
|---|---|---|---|---|
| | 1 | 2 | 3 | 4 |
| Desalting rate | 31% | 54% | 86% | 96% |
| Magnification of concentration | 1.5 | 2.0 | 2.0 | 2.0 |
| Total yield of valuable matters such as α-APM, etec.*[1] | 98.5 | 96.7 | 94.3 | 83.1 |
| III/I + II ratio in treated solution | 1.43 | 0.96 | 0.3 | 0.1 |

*[1] α-APM, α-A(M)PM, α-A(M)P and α-AP

The 4 desalted solutions obtained by the procedure described above were concentrated to 1.65 g/dl and the concentration of the valuable materials, such as α-APM, etc., calculated as total nitrogen content. Each concentrate was charged in a 3-necked flask of 300 ml equipped with a stirrer. Methanol, 6 ml, and 51 ml of 35% hydrochloric acid were added to each concentrate and each mixture was put in a thermostat adjusted to 10° C. to perform crystallization for 3 days with stirring. The precipitated crystals were taken by filtration. After washing with a small amount of cold 2 N hydrochloric acid, the crystals were dried at 50° C. under reduced pressure.

Infrared absorption spectra of these crystals were identical with those of α-APM hydrochloride. The results on yield, recovery rate and purity (liquid chromatography) are shown in Table 5.

TABLE 5

| No. | III/I + II Ratio in Raw Solution | Yield (g) | From Desalted Solution Purity *1*2 | From Mother Liquor from which α-APM was separated | |
|---|---|---|---|---|---|
| | | | | Recovery Rate (1) | Recovery Rate (2) |
| 1 | 1.43 | 39.5 (21.4)*[3] | 69.4 (98.0)*[3] | 70.5 (53.8)*[3] | 69.4 (53.0)*[3] |
| 2 | 0.96 | 27.0 | 98.1 | 68.5 | 66.2 |
| 3 | 0.3 | 25.5 | 98.3 | 64.7 | 61.0 |
| 4 | 0.1 | 23.8 | 98.7 | 60.6 | 50.4 |

*[1] Purity as α-APM hydrochloride
*[2] NH₄Cl content, 29.1%
*[3] Value obtained by adding water until NH₄Cl was completely dissolved.

From this example, it will can be seen that when the III/I+II ratio in the treated solution is greater than 1.0, the obtained crystals are not pure and considerable work is required for re-purification. For this reason, the yield is markedly reduced. On the other hand, it can be seen that also when the III/I+II ratio is lower than 0.3, the valuable material are consequentially shifted to the permeation liquid together with the salts to cause loss of the valuable matters so that decrease in the yield results.

Obviously, numerous modifications and variations of the present invention are possible in light of the above teachings..It is therefore to be understood that within the scope of the appended claims, the invention may be practiced otherwise than as specifically described herein.

What is claimed as new and desired to be secured by Letters Patent of the United States is:

1. A process for recovering the hydrochloride salt of α-L-aspartyl-L-phenylalanine methyl ester from a solution comprising:
   desalting and concentrating a solution containing α-L-aspartyl-L-phenylalanine methyl ester in a vessel provided with a reverse osmosis membrane having a sodium chloride inhibition rate of from 30 to 80%, wherein the said solution contains α-L-aspartyl-L-phenylalanine, α-L-aspartyl-L-phenylalanine methyl ester, the methyl ester at the L-aspartic acid β-carboxyl residue of α-L-aspartyl-L-phenylalanine, the methyl ester at the L-aspartic acid β-carboxy residue of α-L-aspartyl-L-phenylalanine methyl ester, and chloride ions, in the following weight ratios:

$$\frac{(I)}{(II)} = \frac{\alpha\text{-A(M)PM(g)}}{\alpha\text{-AP(g)} + \alpha\text{-APM(g)} + \alpha\text{-A(M)P(g)}} \leq 1$$

$$\frac{(III)}{(I) + (II)} =$$

$$\frac{Cl^-(g)}{\alpha\text{-AP(g)} + \alpha\text{-APM(g)} + \alpha\text{-A(M)P(g)} + \alpha\text{-A(M)PM(g)}} \geq 1$$

wherein:
α-AP is α-L-aspartyl-L-phenylalanine;
α-APM is α-L-aspartyl-L-phenylalanine methyl ester,
α-A(M)P is the methyl ester at the L-aspartic acid β-carboxyl residue of α-L-aspartyl-L-phenylalanine;
α-A(M)PM is the methyl ester at the L-aspartic acid β-carboxyl residue of α-L-aspartyl-L-phenylalanine methyl ester; and
$Cl^{31}$ is chloride ion,
said solution being desalted and concentrated until the weight ratio of inorganic chloride to the sum of α-AP+α-APM+α-A(M)P+α-A(M)PM reaches a ratio of between 0.3 to 1, at which point the concentrate is brought into contact with an aqueous solvent containing methanol and hydrochloric acid to cause the precipitation of the hydrochloride salt of α-APM; and
separating the precipitated hydrochloride salt of α-L-aspartyl-L-phenylalanine methyl ester from the solution.

2. The process of claim 1, wherein said membrane is a polysulfone-, a polyamide- or a cellulose acetate-type reverse osmosis membrane.

3. The process of claim 2, wherein said membrane is polysulfone-type reverse osmosis membrane.

4. The process of claim 2 wherein said membrane is polyamide-type reverse osmosis membrane.

5. The process of claim 2, wherein said membrane is a cellulose-acetate-type reverse osmosis membrane.

6. The process of claim 1, wherein the solution temperature during desalting and concentration ranges from 5° to 50° C.

7. The process of claim 1, wherein the pressure on said solution, during reverse osmosis ranges from 10 to 70 g cm$^{-2}$G$^{-1}$.

8. The process of claim 1, wherein said solution has a pH ranging from 2 to 8.

9. The process of claim 1, wherein the amount of methanol in said aqueous solvent added to said solution ranges from two moles of methanol per liter of desalted solution to one mole of methanol per mole of α-AP.

10. The process of claim 1, wherein the amount of hydrochloric acid added to said solution ranges from about 0.5 to about 5 moles per liter of the salted solution.

11. The process of claim 1, wherein said aqueous solvent, in addition to methanol and hydrochloric acid, contains ethylene glycol or acetone.

12. A process for recovering α-L-aspartyl-L-phenylalanine methyl ester from a solution, comprising:
 desalting and concentrating a solution containing α-L-aspartyl-L-phenylalanine methyl ester in a vessel provided with a reverse osmosis membrane having a sodium chloride inhibttion rate of from 30 to 80%, wherein the said solution contains α-L-aspartyl-L-phenylalanine, α-L-aspartyl-L-phenylalanine methyl ester, the methyl ester at the L-aspartic acid β-carboxyl residue of α-L-aspartyl-L-phenylalanine, the methyl ester at the L-aspartic acid β-carboxy residue of α-L-aspartyl-L-phenylalanine methyl ester, and chloride ions, in the following weight ratios:

$$\frac{(I)}{(II)} = \frac{\alpha\text{-A(M)PM(g)}}{\alpha\text{-AP(g)} + \alpha\text{-APM(g)} + \alpha\text{-A(M)P(g)}} \leq 1$$

$$\frac{(III)}{(I) + (II)} = \frac{Cl^-(g)}{\alpha\text{-AP(g)} + \alpha\text{-APM(g)} + \alpha\text{-A(M)P(g)} + \alpha\text{-A(M)PM(g)}} \leq 1$$

wherein:
α-A- is α-L-aspartyl-L-phenylalanine;
α-APM is α-L-aspartyl-L-phenylalanine methyl ester,
α-A(M)P is the methyl ester at the L-aspartic acid β-carboxyl residue of α-L-aspartyl-L-phenylalanine
α-A(M)PM is the methyl ester at the L-aspartic acid β-carboxyl residue of α-L-aspartyl-L-phenylalanine methyl ester; and
Cl⁻is chloride ion, said solution being desalted and concentrated until the weight ratio of inorganic chloride to the sum of α-AP+α-APM+α-A(M)P+α-A(M)PM reaches a ratio of between 0.3 to 1, at which point the concentrate is brought into contact with an aqueous solvent containing methanol and hydrochloric acid to cause the precipitation of the hydrochloride salt of α-APM; and
 separating the preciptiated hydrochloride salt of α-L-aspartyl-L-phenylalanine methyl ester from the solution,
 neutralizing said separated hydrochloride salt of α-L-aspartyl-L-phenylalanine methyl ester; and
 recovering α-L-aspartyl-L-phenylalanine methyl ester.

13. The process of claim 12, wherein said membrane is a polysulfone-, a polyamide- or a cellulose acetate-type reverse osmosis membrane.

14. The process of claim 13, wherein said membrane is a polysulfone-type reverse osmosis membrane.

15. The process of claim 13, wherein said membrane is a polyamide-type reverse osmosis membrane.

16. The process of claim 13, wherein said membrane is a cellulose-acetate-type reverse osmosis membrane.

17. The process of claim 12, wherein the solution temperature during desalting and concentration ranges from 5° to 50° C.

18. The process of claim 12, wherein the pressure on said solution, during reverse osmosis ranges from 10 to 70 g cm$^{-2}$G$^{-1}$.

19. The process of claim 12, wherein said solution has a pH ranging from 2 to 8.

20. The process of claim 12, wherein the amount of methanol in said aqueous solvent added to said solution ranges from two moles of methanol per liter of desalted solution to one mole of methanol per liter of desalted solution to one mole of methanol per mole of α-AP.

21. The process of claim 12, wherein the amount of hydrochloric acid added to said solution ranges from about 0.5 to about 5 moles per liter of the salted solution.

22. The process of claim 12, wherein said aqueous solvent, in addition to methanol and hydrochloric acid, contains ethylene glycol or acetone.

* * * * *